US009617315B2

(12) United States Patent
Sekiyama et al.

(10) Patent No.: US 9,617,315 B2
(45) Date of Patent: Apr. 11, 2017

(54) ARTIFICIAL POLYPEPTIDE FIBER AND METHOD FOR PRODUCING THE SAME

(75) Inventors: Kazuhide Sekiyama, Tsuruoka (JP); Kaori Sekiyama, Tsuruoka (JP); Mizuki Ishikawa, Tsuruoka (JP); Ryota Sato, Tsuruoka (JP); Shinya Murata, Tsuruoka (JP)

(73) Assignee: SPIBER INC., Yamagata (JP)

( * ) Notice: Subject to any disclaimer, the term of this patent is extended or adjusted under 35 U.S.C. 154(b) by 491 days.

(21) Appl. No.: 14/114,636

(22) PCT Filed: May 30, 2012

(86) PCT No.: PCT/JP2012/063923

§ 371 (c)(1),
(2), (4) Date: Oct. 29, 2013

(87) PCT Pub. No.: WO2012/165476

PCT Pub. Date: Dec. 6, 2012

(65) Prior Publication Data

US 2014/0058066 A1 Feb. 27, 2014

(30) Foreign Application Priority Data

Jun. 1, 2011 (JP) ................................ 2011-123647

(51) Int. Cl.
*C07K 14/435* (2006.01)
*D01F 4/02* (2006.01)
(Continued)

(52) U.S. Cl.
CPC ......... *C07K 14/43518* (2013.01); *D01D 5/06* (2013.01); *D01D 5/16* (2013.01); *D01F 4/02* (2013.01); *D01F 6/68* (2013.01)

(58) Field of Classification Search
CPC ................................................ C07K 14/43518
See application file for complete search history.

(56) References Cited

U.S. PATENT DOCUMENTS 5,171,505 A 12/1992 Lock
5,252,285 A 10/1993 Lock
(Continued)

FOREIGN PATENT DOCUMENTS

CN 1078509 11/1993
CN 1952225 4/2007
(Continued)

OTHER PUBLICATIONS

Xia et al.: "Native-sized recombinant spider silk protein produced in metabolically engineered *Escherichia coli* results in a strong fiber"; PNAS vol. 107, No. 32, pp. 14059-14063, Aug. 10, 2010.
Heim et al.: "Spider Silk: From Soluble Protein to Extraordinary Fiber"; Angewandte Chemie International Edition, vol. 48, No. 20, May 2009, pp. 3584-3596.
(Continued)

*Primary Examiner* — Karen Cochrane Carlson
(74) *Attorney, Agent, or Firm* — Hamre, Schumann, Mueller & Larson, P.C.

(57) ABSTRACT

An artificial polypeptide fiber of the present invention is an artificial fiber containing a polypeptide as a main component, and has a stress of 350 MPa or more and a toughness of 138 MJ/$m^3$ or more. A method for producing an artificial polypeptide fiber of the present invention is a method for producing the artificial polypeptide fiber obtained by spinning a spinning solution (6) containing a polypeptide derived from natural spider silk proteins and performing drawing of at least two stages. The drawing of at least two stages includes a first-stage drawing (3) in wet heat and a second-stage drawing (4) in dry heat. Thereby, the present invention provides high-toughness artificial polypeptide fibers having favorable stress and rupture elongation, and a method for producing the same.

6 Claims, 6 Drawing Sheets

(51) Int. Cl.

| | |
|---|---|
| ***D01F 6/68*** | (2006.01) |
| ***D01D 5/06*** | (2006.01) |
| ***D01D 5/16*** | (2006.01) |

(56) References Cited

U.S. PATENT DOCUMENTS

| | | | |
|---|---|---|---|
| 6,620,917 | B1 | 9/2003 | Mello et al. |
| 7,057,023 | B2 † | 6/2006 | Islam |
| 8,278,416 | B1 | 10/2012 | Johansson et al. |
| 2003/0155670 | A1 | 8/2003 | O'Brien |
| 2004/0102614 | A1 | 5/2004 | Islam et al. |
| 2004/0132957 | A1 | 7/2004 | Asakura |
| 2005/0054830 | A1 | 3/2005 | Islam et al. |
| 2005/0158821 | A1 | 7/2005 | Mello et al. |
| 2009/0226969 | A1 | 9/2009 | Johansson et al. |
| 2009/0318963 | A1 | 12/2009 | Asakura |
| 2012/0329992 | A1 | 12/2012 | Johansson et al. |
| 2013/0172478 | A1 | 7/2013 | Bausch |
| 2014/0245923 | A1 | 9/2014 | Sugahara et al. |

FOREIGN PATENT DOCUMENTS

| | | |
|---|---|---|
| CN | 101705559 | 5/2010 |
| CN | 101724920 | 6/2010 |
| EP | 0559725 | 9/1993 |
| EP | 0816505 | 1/1998 |
| JP | 4-263614 | 9/1992 |
| JP | 5-263312 | 10/1993 |
| JP | 6-502993 | 4/1994 |
| JP | 8-74123 | 3/1996 |
| JP | 2004-503204 | 2/2004 |
| JP | 2005-515309 | 5/2005 |
| JP | 2007/303015 | 11/2007 |
| JP | 2009-521921 | 6/2009 |
| JP | 2010-024586 | 2/2010 |
| JP | 4945768 B | 6/2012 |
| JP | 2012-136795 | 7/2012 |
| WO | WO 92/09695 | 6/1992 |
| WO | WO 01/36531 | 5/2001 |
| WO | WO 01/70973 | 9/2001 |
| WO | WO 2008/004356 | 1/2008 |
| WO | WO 2010/123450 | 10/2010 |
| WO | WO 2011/113592 | 9/2011 |
| WO | WO 2012/165477 | 12/2012 |
| WO | WO 2013/065650 | 5/2013 |
| WO | WO 2013/065651 | 5/2013 |

OTHER PUBLICATIONS

Extended European Search Report, Feb. 9, 2015; European Application No. 12793074.1 (9 pages).

Office Action issued in corresponding Chinese Application No. 201380034158.4, Jul. 27, 2015, 7 pages.

Extended European Search Report issued in corresponding European Application No. 13810001.1, Dec. 18, 2015, 7 pages.

Specification for co-pending U.S. Appl. No. 14/405,101, filed Dec. 2, 2014 (37 pages).

Lazaris et al.: "Spider Silk Fibers Spun from Soluble Recombinant Silk Produced in Mammalian Cells"; Science 295, pp. 472-476, Jan. 18, 2011.

Elices et al.: "Bioinspired Fibers Follow the Track of Natural Spider Silk"; Macromolecules, vol. 44, No. 5, pp. 1166-1176, Apr. 2, 2011.

Agnarsson et al.: "Bioprospecting Finds the Toughest Biological Material: Extraordinary Silk from a Giant Riverine Orb Spider"; PLOS ONE, vol. 5, Issue 9, Sep. 2010.

Tsukada, et al., "Structural Changes and Dyeability of Silk Fibroin Fiber following Shrinkage in Neutral Salt Solution", J. Appl. Polymer Sci, 1994, 51(4), pp. 619-624.

Office Action issued in corresponding Chinese Patent Application No. 201380034158.4, Feb. 29, 2016, 12 page with a partial English translation.

Phipps, et al., "Analysis of Azo Dyes Using a Core Enhanced Technology Accucore HPLC Column", Thermo Scientific, Aug. 2011, pp. 1-2, Retrieved from <https://tools.thermofisher.com/content/sfs/brochures/ANCCSCETAZODYE_0611.pdf> on Oct. 27, 2016.

Lopez-Cortes, et al., "Screening and isolation of PHB-Producing Baceria in a Polluted Marine Microbial Mat", Microb Ecol (2008) 56:112-120. DOI 10.1007/s00248-007-9329-8.

Davies, et al., (2003) "Measurement of Isoketal Protein Adducts by Liquid Chromatography-Electrospray Ionization/Tandem Mass Spectrometry", in Hensley & Ford (Eds.) Methods in Biological Oxidate Stress (Chapter 15, p. 30). Totowa, New Jersey:Humana Press.

Guerette et al., "Silk Properties Determined by Gland-Specific Expression of a Spider Fibroin Gene Family." Science (1996), 112-115.†

Xia et al., "Native-sized recombinant spider silk protein produced in metabolically engineered *Escherichia coli* results in a strong fiber." Proc. Natl. Acad. Sci. (2010), 14059-14063.†

Elices et al., "Bioinspired Fibers Follow the Track of Natural Spider Silk." Macromolecules (2011) 1166-1176.†

† cited by third party

ARTIFICIAL POLYPEPTIDE FIBER AND METHOD FOR PRODUCING THE SAME

TECHNICAL FIELD

The present invention relates to an artificial polypeptide fiber that is one kind of synthetic protein fibers and a method for producing the same.

BACKGROUND ART

Spider silk fibers are fibers having high strength and toughness, and are known to have higher strength and toughness than high-tensile steels, nylon 6 fibers, aramid fibers, carbon fibers, etc. In addition, they have an advantage in that oil is not used as a raw material and biomass can be used instead. Some artificial spider silk fibers also have been proposed. For example, Patent Document 1 has proposed a fiber produced by extruding a synthetic protein spinning solution into a coagulation bath with 90% methanol from a spinneret at a speed of 5 to 10 μl/min. Patent Document 2 has proposed a fiber 1 μm or more in diameter and 5 mm or more in length having a tensile strength of 200 MPa or higher. Non-Patent Document 1 has disclosed a drawn yarn having a strength of 1.91 to 2.26 g/d and an elongation of 43.4 to 59.6% obtained by drawing a yarn at a draw ratio of 5 times in a methanol bath and a water bath. Non-Patent Document 2 has disclosed a drawn yarn having a stress of 600 MPa and an elongation of 25% obtained by drawing a yarn at a draw ratio of 5 times. Non-Patent Document 3 has disclosed a drawn yarn having a stress of 280 to 350 MPa and an elongation of 30 to 40% obtained by keeping a yarn in steam for 5 minutes so as to draw the yarn to 5 times.

However, the toughness of conventional artificial polypeptide fibers is not sufficiently high, and hence tenacious fibers having still higher stress have been desired.

PRIOR ART DOCUMENTS

Patent Documents

Patent Document 1: JP 2004-503204 A
Patent Document 2: JP 2009-521921 A

Non-Patent Documents

Non-Patent Document 1: Anthoula Lazaris, et. al., "Spider Silk Fiber Spun from Soluble Recombinant Silk Produced in Mammalian Cells", Science, 295, page 472, Jan. 18, 2002

Non-Patent Document 2: Xiao-Xia Xia, et. al., "Native-sized recombinant spider silk protein produced in metabolically engineered *Escherichia coli* results in a strong fiber", PNAS, vol. 107, No. 32, pages 14059-14063, Aug. 10, 2010

Non-Patent Document 3: M. Elice, et. al., "Bioinspired Fibers Follow the Track of Natural Spider Silk", Macromolecules, Vol. 44, No. 5, pages 1166-1176, Apr. 2, 2011

DISCLOSURE OF INVENTION

Problem to be Solved by the Invention

In order to solve the above-described conventional problem, the present invention provides an artificial polypeptide fiber having high stress and toughness, and a method for producing the same.

Means for Solving Problem

An artificial polypeptide fiber of the present invention is an artificial fiber containing a polypeptide as a main component, and has a stress of 350 MPa or more and a toughness of 138 MJ/m$^3$ or more.

A method for producing an artificial polypeptide fiber of the present invention is a method for producing an artificial polypeptide fiber that is obtained by spinning a spinning solution containing a polypeptide derived from natural spider silk proteins and performing drawing of at least two stages. The drawing of at least two stages includes a first-stage drawing in wet heat and a second-stage drawing in dry heat.

Effect of the Invention

The present invention can provide an artificial polypeptide fiber having high stress and toughness by drawing an undrawn fiber made of artificial polypeptide through at least two stages in wet heat and dry heat, and a method for producing the same. Specifically, it is possible to realize an artificial polypeptide fiber having a stress of 350 MPa or more and a toughness of 138 MJ/m$^3$ or more. The fiber having high stress and high toughness is advantageous as a composite material formed with metal, resin, rubber, etc.

BRIEF DESCRIPTION OF DRAWINGS

FIG. 2A shows a spinning process and a first-stage drawing process, and FIG. 2B shows a second-stage drawing process.

DESCRIPTION OF THE INVENTION

(1) Polypeptide

Figure 1:
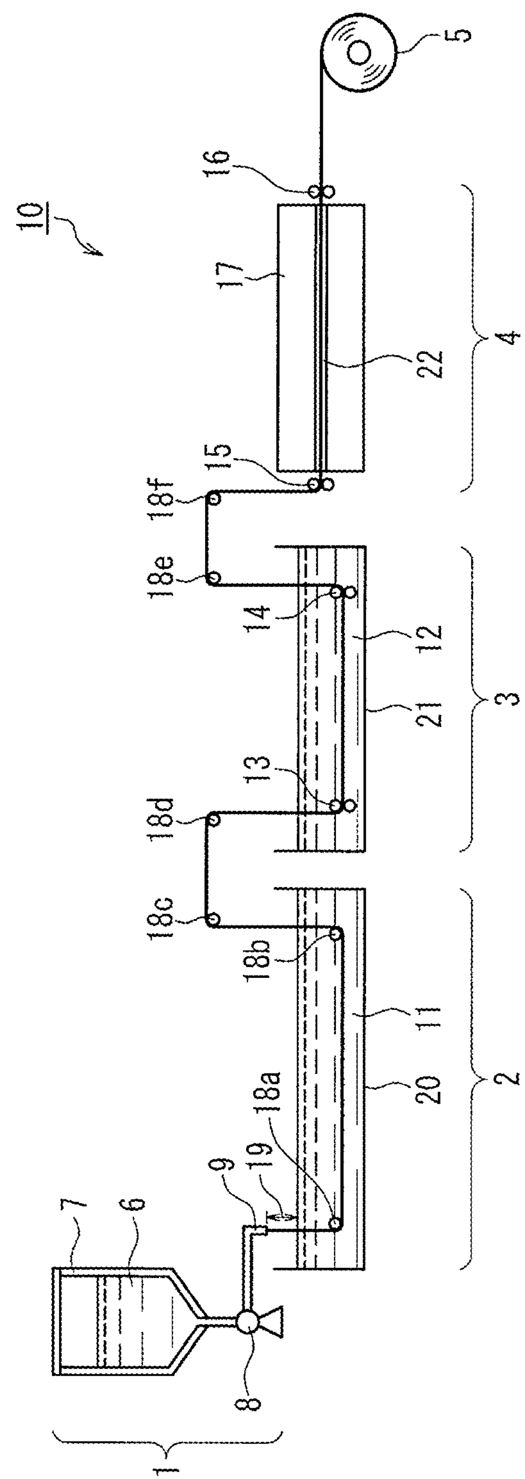
FIG. 1 illustrates a production process in one example of the present invention.

An artificial polypeptide fiber of the present invention contains a polypeptide as a main component. In the present invention, the term "main component" refers to a component contained in an amount of 80% by mass (mass %) or more, more preferably contained in an amount of 90 mass % or more, and further preferably contained in an amount of 95 mass % or more. Incidentally, the artificial polypeptide fiber of the present invention may contain components other than polypeptides within a range that do not inhibit the effect of the present invention. In the present invention, as a raw material, it is desirable to use a polypeptide derived from natural spider silk proteins. Examples of the polypeptide derived from natural spider silk proteins include variants, analogs, derivatives or the like of the natural spider silk proteins. The polypeptide is not limited particularly insofar as it is derived from natural spider silk proteins. In terms of obtaining excellent tenacity, the polypeptide preferably is derived from spigot dragline proteins produced in the major ampullate glands of spiders. Examples of the spigot dragline proteins include major ampullate spidroin MaSp1 and MaSp2 derived from Nephila clavipes, and ADF3 and ADF4 derived from Araneus diadematus, etc. Examples of the polypeptide derived from the spigot dragline proteins include variants, analogs, derivatives or the like of the spigot dragline proteins.

Examples of the polypeptide derived from the spigot dragline proteins include a polypeptide containing two or more units of an amino acid sequence represented by the formula 1:

REP1–REP2 (1), preferably a polypeptide containing five or more units thereof, and more preferably a polypeptide containing ten or more units thereof. Alternatively, the polypeptide derived from the spigot dragline proteins may be a polypeptide that contains units of the amino acid sequence represented by the formula 1:

REP1–REP2 (1)

and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3. Incidentally, in the polypeptide derived from the spigot dragline proteins, units of the amino acid sequence represented by the formula (1):

REP1–REP2 (1)

may be the same or may be different from each other. Here, the units of the amino acid sequence represented by [REP1–REP2 (1)] 1 being different from each other includes cases where the REP1 is different, the REP2 is different, and both of the REP1 and REP2 are different. As to the polypeptide derived from the spigot dragline proteins, when producing a recombinant protein using a microbe such as *Escherichia coli* as a host, the molecular weight is preferably 300 kDa or less, more preferably 200 kDa or less, and further preferably 150 kDa or less, in view of productivity.

In the formula (1) above, the REP1 is an amino acid sequence composed of 2 to 20 amino acid residues arranged in series that are selected from at least one of alanine and glycine, more preferably 3 to 16 amino acid residues arranged in series selected therefrom, further preferably 4 to 12 amino acid residues arranged in series selected therefrom, and most preferably 5 to 8 amino acid residues arranged in series selected therefrom. In the formula (1) above, the REP2 is an amino acid sequence composed of 2 to 200 amino acid residues, more preferably 10 to 150 amino acid residues, further preferably 20 to 100 amino acid residues and most preferably 20 to 75 amino acid residues, and the total number of glycine, serine, glutamine and alanine residues contained in the amino acid sequence is 40% or more, preferably 60% or more, and more preferably 70% or more with respect to the total number of amino acid residues contained therein.

In the spigot dragline, the above REP1 corresponds to a crystal region in a fiber where a crystal β sheet is formed, and the above REP2 corresponds to an amorphous region in a fiber where most of parts lack regular configurations and that has more flexibility. Further, the above [REP1–REP2] corresponds to a repetitious region (repetitive sequence) composed of the crystal region and the amorphous region, which is a characteristic sequence of dragline proteins.

An amino acid sequence represented by SEQ ID NO: 1 is identical to an amino acid sequence that is composed of 50 amino acid residues of an amino acid sequence of ADF3 (GI: 1263287, NCBI) from the C-terminal. An amino acid sequence represented by SEQ ID NO: 2 is identical to an amino acid sequence represented by SEQ ID NO: 1 in which 20 amino acid residues have been removed from the C-terminal. An amino acid sequence represented by SEQ ID NO: 3 is identical to an amino acid sequence represented by SEQ ID NO: 1 in which 29 amino acid residues have been removed from the C-terminal.

An example of the above-described polypeptide that contains units of the amino acid sequence represented by the formula 1:

REP1–REP2 (1)

and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3 is a polypeptide having an amino acid sequence represented by SEQ ID NO: 4. The polypeptide having an amino acid sequence represented by SEQ ID NO: 4 is one obtained by the following mutation: in an amino acid sequence of ADF3 to which an amino acid sequence (SEQ ID NO: 7) composed of a start codon at a N-terminal, His 10 tags and an HRV3C Protease (Human rhinovirus 3C Protease) recognition site has been added, $1^{st}$ to $13^{th}$ repetitive regions are about doubled and the translation ends at the $1154^{th}$ amino acid residue. In the polypeptide having the amino acid sequence represented by SEQ ID NO: 4, the C-terminal sequence is identical to the amino acid sequence represented by SEQ ID NO: 3.

Further, another example of the above-described polypeptide that contains units of the amino acid sequence represented by the formula 1:

REP1–REP2 (1)

and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3 is a protein that has an amino acid sequence represented by SEQ ID NO: 4 in which one or a plurality of amino acids have been substituted, deleted, inserted and/or added and that has the repetitious region composed of the crystal region and the amorphous region. In the present invention, "one or a plurality of" refers to 1 to 40, 1 to 35, 1 to 30, 1 to 25, 1 to 20, 1 to 15, 1 to 10, or 1 or a few, for example. Further, in the present invention, "one or a few" refers to 1 to 9, 1 to 8, 1 to 7, 1 to 6, 1 to 5, 1 to 4, 1 to 3, 1 to 2, or 1.

The polypeptide can be produced using a host that has been transformed by an expression vector containing a gene encoding a polypeptide. A method for producing a gene is not limited particularly, and it may be produced by amplifying a gene encoding a natural spider silk protein from a cell derived from spiders by a polymerase chain reaction (PCR) or the like for cloning, or may be synthesized chemically. A method for chemically synthesizing a gene also is not limited particularly, and it can be synthesized as follows, for example: based on information of amino acid sequences of natural spider silk proteins obtained from the NCBI web database, etc., oligonucleotides that have been synthesized automatically with AKTA oligopilot plus 10/100 (GE Healthcare Japan Corporation) are linked by PCR or the like. At this time, in order to facilitate the purification and observation of protein, it is possible to synthesize a gene that encodes a protein having an amino acid sequence of the above-described amino acid sequence to which an amino acid sequence composed of a start codon and His 10 tags has been added, to the N-terminal. Examples of the expression vector include a plasmid, a phage, a virus, etc., that can express protein from a DNA sequence. The plasmid type expression vector is not limited particularly insofar as it allows expression of a target gene in a host cell and it can amplify itself. For example, in the case of using *Escherichia coli* Rosetta (DE3) as a host, a pET22b(+) plasmid vector, a pCold plasmid vector and the like can be used. Among these, in view of productivity of protein, it is preferable to use the pET22b(+) plasmid vector. Examples of the host include animal cells, plant cells, microbes, etc.

(2) Spinning Solution

A spinning solution (dope solution) is prepared by adding a solvent to the above-described polypeptide and adjusting the viscosity to allow spinning. The solvent is not limited particularly insofar as it can dissolve the polypeptide. For example, if the polypeptide is derived from Araneus diadematus, as an example, a solution containing hexafluoroisopropanol (HFIP), hexafluoroacetone (HFA), formic acid, urea, guanidine, sodium dodecyl sulfate (SDS), lithium bromide, calcium chloride, lithium thiocyanate or the like is used as a solvent and the solvent is added to the polypeptide in an appropriate amount so that the viscosity of the solution becomes 100 to 10,000 cP (centipoises). This is defined as the spinning solution.

(3) Spinning

Wet spinning is adopted as the spinning. By this method, the solvent dissolving a polymer is removed (also called as desolvation) and an undrawn yarn is obtained. A coagulation liquid to be used for the wet spinning is not limited particularly insofar as it allows desolvation. When the solvent is HFIP, the coagulation liquid preferably is a lower alcohol with a carbon number of 1 to 5 such as methanol, ethanol and 2-propanol, or acetone. The temperature of the coagulation liquid preferably is 0-30° C. This range stabilizes spinning. By extruding the spinning solution into the coagulation liquid, an undrawn yarn is obtained. When using a syringe pump with a nozzle 0.1-0.6 mm in diameter, the extrusion speed preferably is set at 0.2-2.4 ml/h per one hole. This range stabilizes spinning. The further preferable extrusion speed is 0.6-2.2 ml/h per one hole. It is preferable that a length of a coagulation liquid bath is 200-500 mm, a take-up speed of the undrawn yarn is 1-3 m/min, and residence time is 0.01-0.15 min. These ranges allow efficient desolvation. Drawing (pre-drawing) may be performed in the coagulation liquid. However, taking into consideration the evaporation of a lower alcohol, it is preferable to maintain the coagulation liquid at low temperature so as to take up yarns in an undrawn state.

(4) Drawing (a) Function of Multistage Drawing

Drawing is performed in at least two stages. Of course, it also is possible to adopt multistage drawing with three or more stages. In the present invention, the reason for adopting the multistage drawing of two or more stages is as follows. Since molecules of polypeptides derived from natural spider silk proteins are less likely to be oriented, the multistage drawing is performed so as to orient the molecules stepwise and increase the total draw ratio. Consequently, high-toughness fibers can be obtained.

(b) Contents of Multistage Drawing

The drawing of at least two stages includes a first-stage drawing in wet heat and a second-stage drawing in dry heat. The first-stage drawing in wet heat may be performed in the above-described coagulation liquid. When adopting the multistage drawing of three or more stages, it is possible to adopt a method of, for example, dividing the first-stage drawing in wet heat into two stages and/or dividing the second-stage drawing in dry heat into two stages. The wet heat of the first-stage drawing may be performed in hot water or by steam heating. An organic solvent, etc., may be added to the hot water. The multistage drawing may include a drawing method other than the wet heat or dry heat in any stage of the drawing process.

(c) Drawing Conditions for First and Second Stages

In the first-stage drawing, it is preferable to draw an undrawn yarn to 2 to 8 times in hot water at 50-90° C. This allows stable drawing. In the second-stage drawing, it is preferable to draw a yarn to 1.25 to 3 times in dry heat at 170-270° C. This provides a high-toughness drawn yarn. In the first-stage drawing described above, it is further preferable to draw an undrawn yarn in hot water at 75-85° C. The draw ratio of the first-stage drawing further preferably is to 2.3 to 7 times. In the second-stage drawing, the dry heat further preferably is set at 180-230° C. The draw ratio of the second-stage drawing further preferably is to 1.35 to 3 times. For improving the toughness of drawn yarns and obtaining them stably, the total draw ratio is preferably to more than 5 times and 20 times or less, and further preferably to 6 times or more and 11 times or less. As an example, the dry heat is performed using an electric tubular furnace or a heat plate.

(d) Continuous Process

The spinning and drawing may be performed as a continuous process or may be divided into any combination of processes. FIG. 1 illustrates a production process in one example of the present invention. FIG. 1 shows a continuous process. A spinning-drawing apparatus 10 includes an extrusion process 1, an undrawn-yarn production process 2, a wet-heat drawing process 3, and a dry-heat drawing process 4. A spinning solution 6 is stored in a storage tank 7 and extruded from a gear pump 8 to a spinneret 9. In a laboratory scale, a spinning solution may be filled in a cylinder and extruded from a nozzle using a syringe pump. The extruded spinning solution is supplied directly or via an air gap 19 into a coagulation liquid 11 of a coagulation liquid bath 20, and thus a solvent is removed. Then, an obtained yarn is supplied into hot water 12 in a drawing bath 21 and subjected to the first-stage drawing. The drawing depends on a speed ratio between a supply nip roller 13 and a take-up nip roller 14. Next, the yarn is supplied to a dry-heat drawing machine 17 and subjected to the second-stage drawing inside a guide 22, whereby a yarn roll 5 is obtained. The drawing depends on a speed ratio between a supply nip roller 15 and a take-up nip roller 16. **18*a* to 18*f*** are yarn guides.

(e) Separated Process

Figure 2A:
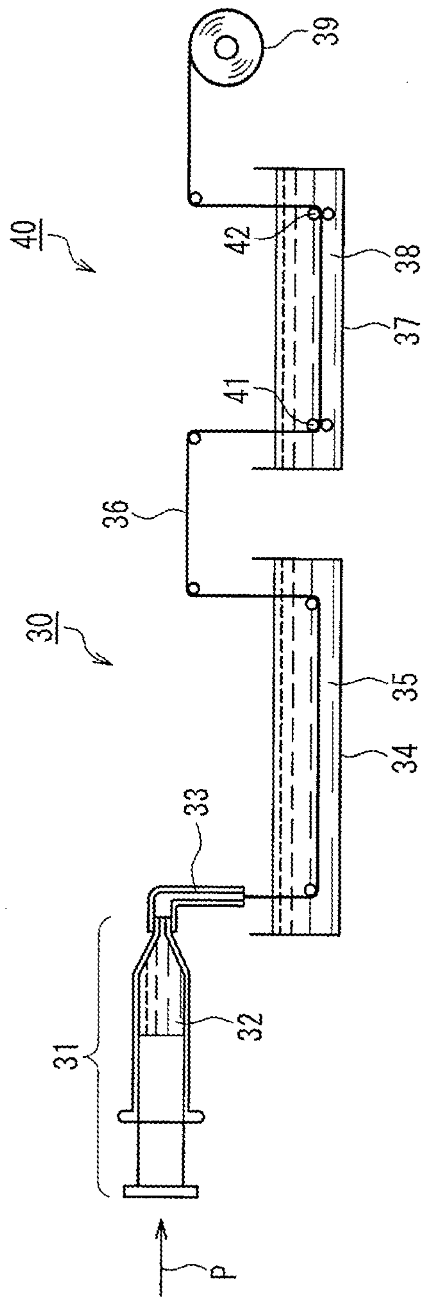
FIGS. 2A and 2B illustrate a production process in another example of the present invention.
Figure 2B:
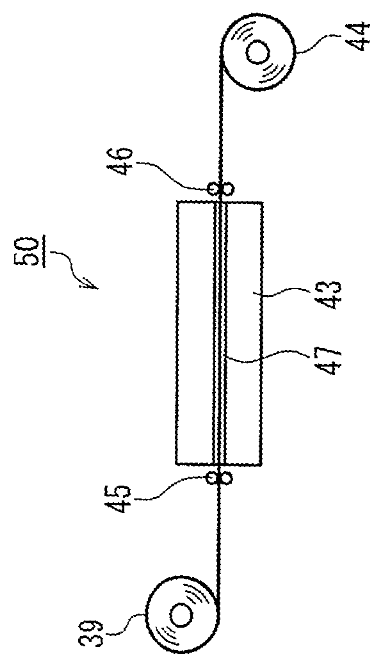

FIGS. 2A and 2B illustrate a case in which the production process is separated in another example of the present invention. FIG. 2A shows a spinning process 30 and a first-stage drawing process 40, and FIG. 2B shows a second-stage drawing process 50. In each process, a yarn may be wound or may be stored in a container without being wound. In the spinning process 30, a spinning solution 32 is contained in a microsyringe 31 and moved in a direction indicated by an arrow P using a syringe pump, so that the spinning solution 32 is extruded from a nozzle 33 and supplied into a coagulation liquid 35 in a coagulation liquid bath 34. Thus, an undrawn yarn 36 is obtained. Then, in the first-stage drawing process 40, the undrawn yarn 36 is supplied into hot water 38 of a drawing bath 37 and subjected to the first-stage drawing, whereby a yarn roll 39 of the first-stage drawn yarn is obtained. The drawing depends on a speed ratio between a supply nip roller 41 and a take-up nip roller 42. Next, the first-stage drawn yarn is unwound from the yarn roll 39, supplied to a dry-heat drawing machine 43, and subjected to the second-stage drawing inside a guide 47. The drawing depends on a speed ratio between a supply nip roller 45 and a take-up nip roller 46. Then, the drawn yarn is wound as a yarn roll 44.

Figure 3:
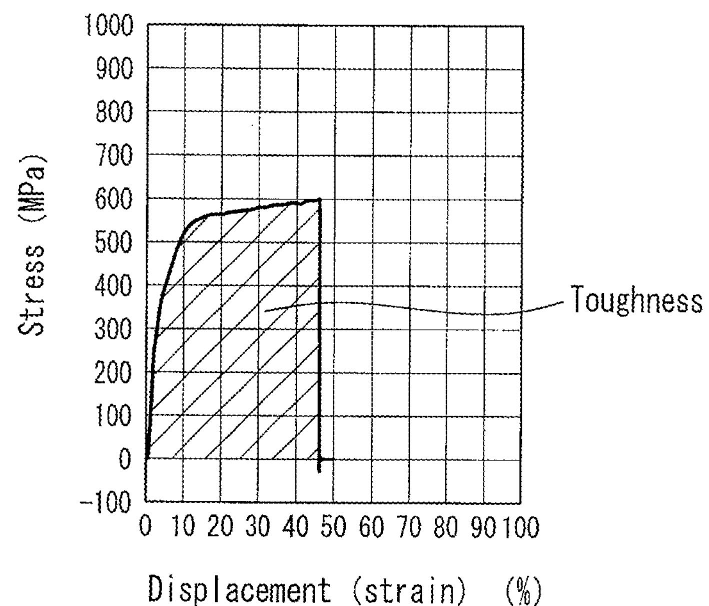
FIG. 3 shows a stress-displacement (strain) curve of a fiber obtained in Example 1 of the present invention.

In the above-described manner, an artificial polypeptide fiber is obtained. The obtained artificial polypeptide fiber has a stress of 350 MPa or more and a toughness of 138 MJ/m$^3$ or more. The toughness is calculated from an integral value of a stress-strain curve (SS curve) at the time of measuring the strength elongation of the fiber. FIG. 3 illustrates the toughness of the fiber obtained in one example of the present invention, and shows a stress-displacement (strain) curve and toughness (shaded part). This indicates that, when the stress and rupture elongation are both high, the toughness also is high.

The stress of the artificial polypeptide fiber of the present invention is preferably 400 MPa or more, more preferably 590 MPa or more, and particularly preferably 620 MPa or more. The rupture elongation is preferably 39% or more, more preferably 45% or more, and further preferably 50% or more. The toughness is preferably 170 MJ/m$^3$ or more, more preferably 240 MJ/m$^3$ or more, and further preferably 260 MJ/m$^3$ or more. An initial elastic modulus of the artificial polypeptide fiber of the present invention is preferably 8 GPa or more, more preferably 14 GPa or more, and further preferably 16 GPa or more.

The diameter of the artificial polypeptide fiber of the present invention preferably ranges from 5 to 100 μm. This range allows the stable supply of drawn yarns. The fiber diameter more preferably ranges from 7 to 30 μm, and further preferably ranges from 8 to 25 μm. Moreover, it is preferable that the diameter of the artificial polypeptide fiber of the present invention is uniform and the variation of the fiber diameter is 5% or less. When the fiber is round in cross section, the fineness (unit: tex or deci tex) is calculated from a cross-sectional area calculated from the fiber diameter, a specific gravity and a length. Incidentally, since the artificial polypeptide fiber of the present invention is obtained by wet spinning, the cross section is not limited to the round shape and may have various shapes. Therefore, the fiber diameter (average diameter) as used herein refers to an average diameter based on the assumption that the cross section is round.

The polypeptide preferably is a polypeptide derived from ADF3 that is one of two major dragline proteins of Araneus diadematus. This polypeptide has advantages of basically having high strength elongation and toughness and being synthesized easily.

A birefringence Δn (×1000) of the artificial polypeptide fiber preferably is 15.6 or more. Incidentally, the birefringence and a birefringence degree are the same. The birefringence can be measured using a compensator called Senarmont, which is a polarizing microscope manufactured by Olympus Corporation. The measurement range is 0 to 546 nm (0 to 1λ). The birefringence is obtained by calculating the formula:

$$\Delta n = R/\text{diameter}.$$

In this formula, R represents a retardation amount (nm) measured by the Senarmont compensator. The birefringence Δn (×1000) of 15.6 or more indicates that the orientation of molecules is progressing.

As to the artificial polypeptide fiber of the present invention after drawing, chemical cross-links may be formed between polypeptide molecules in a fibroin fiber. Examples of functional groups that can be used for cross-links in the polypeptide include amino groups, carboxyl groups, thiol groups and hydroxy groups, but they are not limited to these. An amino group of a lysine side chain contained in the polypeptide can be cross-linked with a carboxyl group of a glutamic acid or an aspartic acid side chain by amide bonds by dehydration condensation. Cross-links may be formed by a dehydration condensation reaction under vacuum heating, or by a dehydration condensation agent such as carbodiimide. Further, a cross-linking agent such as glutaraldehyde also may be used. Further, an enzyme such as transglutaminase may be used to form cross-links. As an example, the cross-linking reaction may be caused using the cross-linking agent such as carbodiimide, glutaraldehyde, etc. Carbodiimide is represented by the general formula:

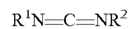

$$R^1N{=}C{=}NR^2$$

(where R$^1$ and R$^2$ indicate an organic group containing an alkyl group with a carbon number of 1 to 6, or a cycloalkyl group), and specific compounds thereof include 1-ethyl-3-(3-dimethylaminopropyl) carbodiimide hydrochloride (EDC), N,N'-dicyclohexylcarbodiimide (DCC), 1-cyclohexyl-3-(2-morpholinoethyl)carbodiimide, diisopropyl carbodiimide (DIC), etc. Among these, EDC and DIC are preferred because peptide chains have high ability of forming amide bonds and thus the cross-linking reaction occurs easily. A cross-linking treatment is performed preferably by applying the cross-linking agent to drawn yarns and forming cross-links by vacuum heating-drying. The cross-linking agent may be applied to fibers in a pure form or may be diluted to the concentration of 0.005 to 10 mass % using a lower alcohol with a carbon number of 1 to 5, a buffer solution, etc. Regarding conditions for the treatment, it is preferable that the temperature is 20 to 45° C. and the time is 3 to 42 hours. The cross-linking treatment using the cross-linking agent allows artificial polypeptide drawn fibers to have further high stress (strength).

EXAMPLES

Hereinafter, the present invention will be described in further detail by way of examples. It should be noted that the present invention is not limited to the following examples.

Examples 1-5

Comparative Examples 1-2

Gene Synthesis (1) Gene Synthesis of ADF3Kai

Part of the amino acid sequence of ADF3 (GI: 1263287), which is one of two major dragline proteins of Araneus diadematus, was obtained from the NCBI web database, and synthesis of a gene encoding an amino acid sequence (SEQ ID NO: 5) was outsourced to GenScript, Inc. The amino acid sequence (SEQ ID NO: 5) is one obtained by adding an amino acid sequence (SEQ ID NO: 7) composed of a start codon at a N-terminal, His 10 tags and an HRV3C Protease (Human rhinovirus 3C Protease) recognition site, to the said amino acid sequence of ADF3. Consequently, a pUC57 vector to which a gene of ADF3Kai having a base sequence represented by SEQ ID NO: 8 had been introduced was obtained (having an Nde I site immediately upstream of 5' terminal of gene and an Xba I site immediately downstream of 5' terminal of gene). Then, the gene was subjected to a restriction enzyme treatment with Nde I and EcoR I, and recombined into a pET22b(+) expression vector.

(2) Gene Synthesis of ADF3Kai-Large

With ADF3Kai used as a template, the PCR reaction was performed using a T7 promoter primer (SEQ ID NO: 11) and a Rep Xba I primer (SEQ ID NO: 12). The half of the genome sequence of ADF3Kai on the 5' side (hereinafter, referred to as a sequence A) was amplified, and the fragment was recombined into a pUC118 vector that in advance had been subjected to the restriction enzyme treatment with Nde I and Xba I using a Mighty Cloning Kit (manufactured by TAKARA BIO INC.). Similarly, with ADF3Kai used as a template, the PCR reaction was performed using an Xba I Rep primer (SEQ ID NO: 13) and a T7 terminator primer (SEQ ID NO: 14). The half of the genome sequence of ADF3Kai on the 3' side (hereinafter, referred to as a sequence B) was amplified, and the fragment was recombined into a pUC118 vector that in advance had been subjected to the restriction enzyme treatment with Xba I and EcoR I using the Mighty Cloning Kit (manufactured by TAKARA BIO INC.). The pUC118 vector to which the sequence A had been introduced and the pUC118 vector to which the sequence B had been introduced were subjected to the restriction enzyme treatment with Nde I, Xba I and Xba I, EcoR I, respectively, and target DNA fragments of the sequences A and B were purified by gel cut. The DNA fragments A, B and the pET22b(+) that in advance had been subjected to the restriction enzyme treatment with Nde I and EcoR I were subjected to a ligation reaction and transformed into *Escherichia coli* DH5α. After confirming the insertion of the target DNA fragments by a colony PCR using a T7 promoter primer and a T7 terminator primer, plasmid was extracted from a colony where a target band size (3.6 kbp) was obtained, and the entire base sequence was checked by a sequence reaction using a 3130×1 Genetic Analyzer (Applied Biosystems). Consequently, the construction of a gene of ADF3Kai-Large represented by SEQ ID NO: 9 was confirmed. Incidentally, the amino acid sequence of ADF3Kai-Large was as represented by SEQ ID NO: 6.

(3) Gene Synthesis of ADF3Kai-Large-NRSH1

With a pET22b(+) vector to which the gene of ADF3Kai-Large obtained above had been introduced used as a template, by means of Site-Directed Mutagenesis using a PrimeSTAR Mutagenesis Basal Kit (manufactured by TAKARA BIO INC.), a codon GGC corresponding to the 1155$^{th}$ amino acid residue, i.e., glycine (Gly), in the amino acid sequence of ADF3Kai-Large (SEQ ID NO: 6) was mutated into a stop codon TAA, and a gene of ADF3Kai-Large-NRSH1 represented by SEQ ID NO: 10 was constructed on the pET22b (+). The accuracy of the introduction of the mutation was checked by the sequence reaction using the 3130×1 Genetic Analyzer (Applied Biosystems). Incidentally, the amino acid sequence of ADF3Kai-Large-NRSH1 was as represented by SEQ ID NO: 4.

<Expression of Protein>

The pET22b(+) expression vector containing the genome sequence of ADF3Kai-Large-NRSH1 obtained above was transformed into *Escherichia coli* Rosetta (DE3). The obtained single colony was grown for 15 hours in an LB culture medium (2 mL) containing ampicillin. Then, the culture solution (1.4 ml) was added to an LB culture medium (140 mL) containing ampicillin, and grown to an $OD_{600}$ of 3.5 under conditions of 37° C. and 200 rpm. Next, the culture solution with the $OD_{600}$ of 3.5 was added together with 50% glucose (140 mL) to a 2×YT culture medium (7 L) containing ampicillin, and grown further to the $OD_{600}$ of 4.0. Then, isopropyl-β-thiogalactopyranoside (IPTG) was added to the obtained culture solution with the $OD_{600}$ of 4.0 so that the final concentration became 0.5 mM, thereby inducing the expression of protein. After a lapse of two hours from the addition of IPTG, the culture solution was centrifuged and bacterial cells were collected. Protein solutions prepared from the culture solutions before and after the addition of IPTG were electrophoresed in a polyacrylamide gel. As a result, a target band size (about 101.1 kDa) was observed with the addition of IPTG, and the expression of the target protein was confirmed.

<Purification>

The bacterial cells collected two hours after the addition of IPTG were washed in a 20 mM Tris-HCl buffer (pH 7.4). The bacterial cells after washing were suspended in a 20 mM Tris-HCl buffer solution (pH 7.4) containing PMSF (about 1 mM) and broken with a high-pressure homogenizer (GEA Niro Soavi). The broken cells were centrifuged and a precipitate was obtained. The obtained precipitate was washed in a 20 mM Tris-HCL buffer solution (pH 7.4) until it achieved high purity. The precipitate after washing was dissolved in a 7.5 M Urea DB buffer solution (7.5 M urea, 10 mM sodium dihydrogen phosphate, 20 mM NaCl, mM Tris-HCl, pH 7.0) and stirred with a stirrer, and then was dialyzed in water using a dialysis tube (cellulose tube 36/32 manufactured by Sanko Junyaku Co., Ltd.). White aggregate protein obtained after dialysis was collected by centrifugation, water was removed by a freeze dryer, and freeze-dried powder was collected. A degree of purification of the target protein (about 101.1 kDa) in the obtained freeze-dried powder was checked by performing an image analysis of the results of polyacrylamide gel powder electrophoresis using Totallab (nonlinear dynamics Ltd.). As a result, the degree of purification of ADF3Kai-Large-NRSH1 was about 85%.

(4) Spinning Solution (Dope Solution)

Hexafluoroisopropanol (HFIP) was added to the freeze-dried powder so that the concentration of the freeze-dried powder became 8.1 mass %. After 14 hours of dissolution using a rotator, dusts and bubbles were removed. The viscosity of the solution was 1,200 cp (centipoises). The obtained solution was defined as the spinning solution (dope solution).

(5) Spinning Process—First-Stage Drawing Process

The method shown in FIGS. 2A and 2B was adopted as the spinning process and the drawing process. The spinning solution was filled in a cylinder and extruded into 100 mass % methanol coagulation liquid from a nozzle 0.2 mm in diameter using a syringe pump. Thus, undrawn yarns were produced. The extrusion speed was set at 1.8 ml/h, and the length of the coagulation liquid bath was 400 mm. Then, as the first-stage drawing, the undrawn yarns were drawn to 2.3 to 7 times in hot water at 80° C. The winding speed was 2.3 to 3.6 m/min.

(6) Second-Stage Drawing Process

It was found that high-toughness drawn yarns were obtained if they were drawn to 1.4 to 2.96 times in the second-stage drawing by a dry heat plate at 180° C.-220° C. In the respective Examples and Comparative Examples, conditions shown in Table 1 below were adopted.

TABLE 1

| | First-stage drawing | | | Second-stage drawing | | |
|---|---|---|---|---|---|---|
| Experimental No. | Temperature of hot water (° C.) | Draw ratio (times) | Winding speed (m/min) | Temperature of dry heat plate (° C.) | Draw ratio (times) | Winding speed (m/min) |
| Ex. 1 | 80 | 7 | 2.3 | 220 | 1.5 | 3.45 |
| Ex. 2 | 80 | 4.5 | 2.3 | 220 | 1.4 | 3.22 |
| Ex. 3 | 80 | 2.3 | 2.3 | 220 | 2.96 | 8.3 |
| Ex. 4 | 80 | 2.5 | 3.5 | 180 | 2.5 | 8.5 |
| Ex. 5 | 80 | 2.6 | 3.6 | 180 | 2.4 | 8.5 |
| Comp. Ex. 1 | 75 | 8 | 2.3 | — | — | — |
| Comp. Ex. 2 | — | — | — | 180 | 3.3 | 2.3 |

(7) Measurement of Properties (a) The surface structure was observed with a scanning electron microscope.

(b) For checking the orientation of molecules, a retardation, an interference color and a birefringence degree were measured using a polarizing microscope manufactured by Olympus Corporation, which is a compensator called Senarmont. The measurement range was from 0 to 546 nm (0 to 1λ), and the birefringence was obtained by calculating the formula:

$$\Delta n = R/\text{diameter}.$$

In this formula, R represents a retardation amount (nm) measured by the Senarmont compensator. The birefringence Δn (×1000) of the fiber of Example 1 was 15.6. Thus, it was confirmed that the orientation of molecules of the fiber of Example 1 was progressing.

(c) The fiber diameter was measured using an optical microscope.

(d) The strength (stress), the initial elastic modulus (obtained based on the measurement of inclinations of 20 points: specifically, inclinations were measured at 20 points with an interval of 50 msec and the maximum inclination was defined as the initial elastic modules), and the elongation (displacement at rupture point, displacement) of the fiber were measured using a tensile tester (small table-top tester EZ-S manufactured by Shimadzu Corporation) under an ambient temperature of 25° C. and a relative humidity of 60%, and the toughness was calculated from the formula below. The sample was attached to a cardboard form, a distance between grippers was 20 mm, and a tensile speed was 10 mm/min. A load cell capacity was 1 N, and the gripper was a clip type. A measured value was an average of five samples (n=5).

$$\text{Toughness} = [E/(r^2 \times \Pi \times L) \times 1000] (\text{unit: MJ/m}^3),$$

where

E fracture energy (unit: J)

r fiber radius (unit: mm)

π pi

L distance between grippers at the time of tensile test measurement: 20 mm (e) The specific gravity measurement of the fiber was outsourced to KAKEN TEST CENTER. The measurement was performed in accordance with JIS L 1015, the float-and-sink method. The specific gravity of the fiber was 1.34.

Table 2 summaries various properties of the fibers. The stress-displacement (strain) curves of the fibers obtained in Examples and Comparative Examples are shown in FIGS. 3-9, respectively.

TABLE 2

Figure 4:
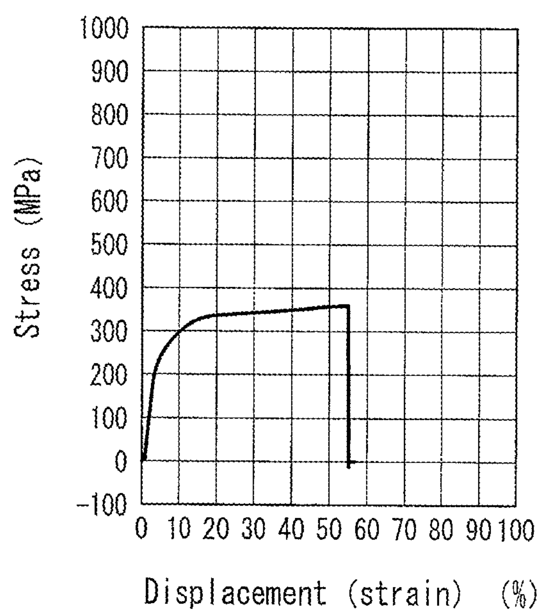
FIG. 4 shows a stress-displacement (strain) curve of a fiber obtained in Example 2 of the present invention.
Figure 5:
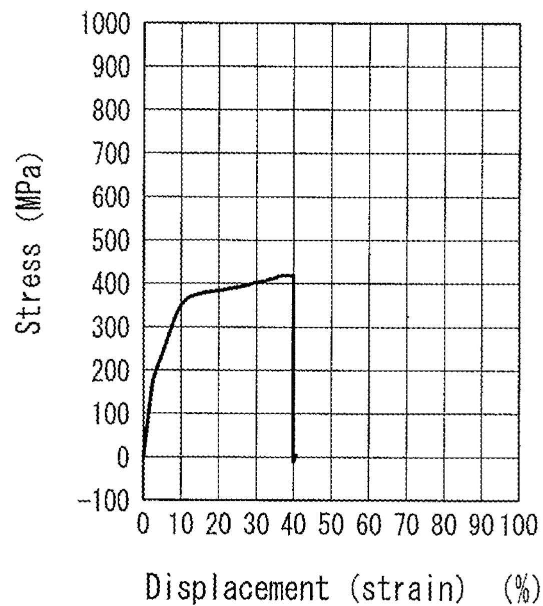
FIG. 5 shows a stress-displacement (strain) curve of a fiber obtained in Example 3 of the present invention.
Figure 6:
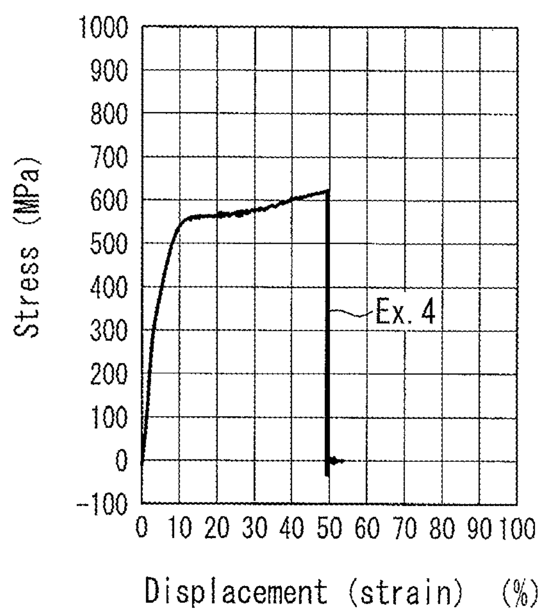
FIG. 6 shows a stress-displacement (strain) curve of a fiber obtained in Example 4 of the present invention.
Figure 7:
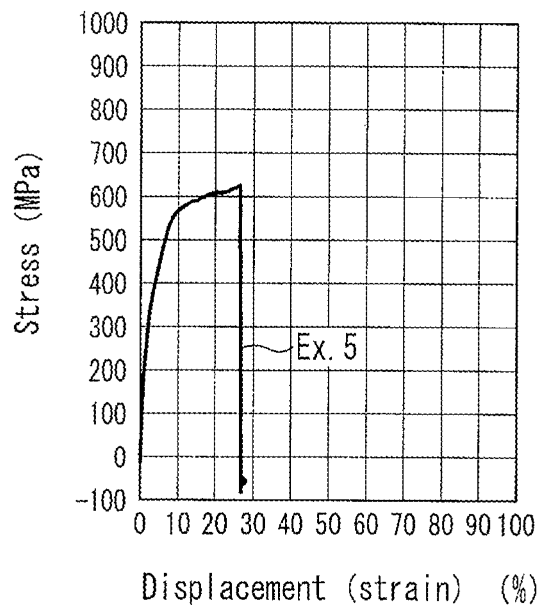
FIG. 7 shows a stress-displacement (strain) curve of a fiber obtained in Example 5 of the present invention.
Figure 8:
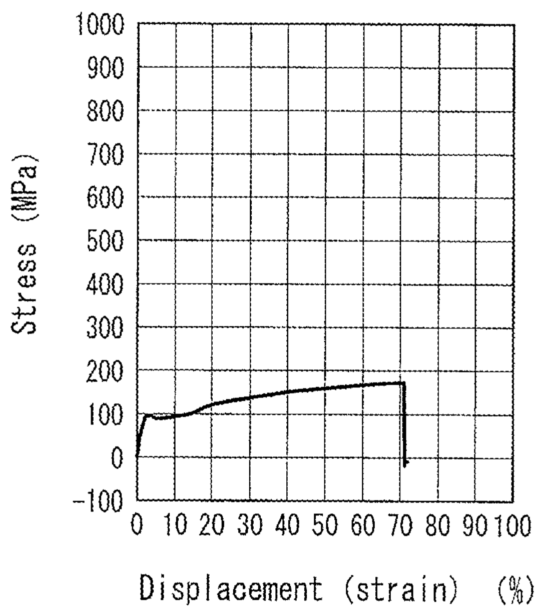
FIG. 8 shows a stress-displacement (strain) curve of a fiber obtained in Comparative Example 1.
Figure 9:
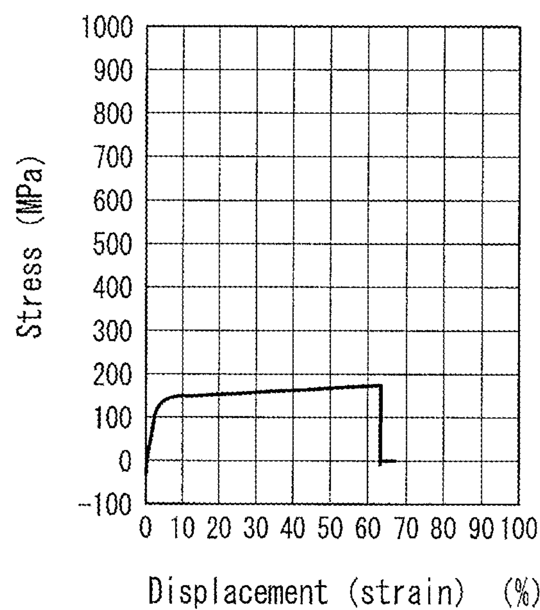
FIG. 9 shows a stress-displacement (strain) curve of a fiber obtained in Comparative Example 2.

| Experimental No. | Stress (MPa) | Stress (cN/dtex) | Initial elastic modulus (GPa) | Displacement at rupture point (strain)(%) | Fiber diameter (μm) | Fineness (tex) | Fracture energy (J) | Toughness (MJ/m³) | Illustration of stress-strain curve |
|---|---|---|---|---|---|---|---|---|---|
| Ex. 1 | 598.4 | 4.5 | 16.1 | 45.5 | 19 | 0.46 | 0.00137 | 241.7 | FIG. 3 |
| Ex. 2 | 357.7 | 2.7 | 9.4 | 54.3 | 24 | 0.59 | 0.00157 | 173.6 | FIG. 4 |
| Ex. 3 | 420.0 | 3.2 | 8.6 | 39.4 | 15 | 0.37 | 0.00049 | 138.7 | FIG. 5 |
| Ex. 4 | 626.4 | 4.7 | 14.5 | 48.6 | 12 | 0.30 | 0.00060 | 265.4 | FIG. 6 |
| Ex. 5 | 628.7 | 4.7 | 17.8 | 26.7 | 11 | 0.27 | 0.00027 | 142.1 | FIG. 7 |
| Comp. Ex. 1 | 174.7 | 1.3 | 5.0 | 71.3 | 31 | 0.77 | 0.00148 | 98.1 | FIG. 8 |
| Comp. Ex. 2 | 174.8 | 1.3 | 5.8 | 62.6 | 25 | 0.61 | 0.00095 | 96.8 | FIG. 9 |

As is apparent from Table 2, it was confirmed that products of Examples of the present invention are high-toughness artificial polypeptide fibers having favorable stress and rupture elongation.

Table 3 summaries the stress, the elongation and the toughness of the fibers obtained in Examples 1-5 of the present invention, and of a conventional natural spider silk fiber, a carbon fiber and a para-based aramid fiber.

TABLE 3

| | Stress (MPa) | Elongation (%) | Toughness (MJ/m³) |
|---|---|---|---|
| Fiber of Ex. 1 of present invention | 598.4 | 45.5 | 241.7 |
| Fiber of Ex. 2 of present invention | 357.7 | 54.3 | 173.6 |
| Fiber of Ex. 3 of present invention | 420.0 | 39.4 | 138.7 |
| Fiber of Ex. 4 of present invention | 626.4 | 48.6 | 265.4 |
| Fiber of Ex. 5 of present invention | 628.7 | 26.7 | 142.1 |
| Natural spider silk fiber | 1,100.0 | 27.0 | 160.0 |
| Carbon fiber | 4,000.0 | 1.3 | 25.0 |
| Aramid fiber (para-based) | 3,600.0 | 2.7 | 50.0 |

(Remarks)

"Displacement at rupture point (strain)" in Table 2 and "Elongation" in Table 3 are the same.

As is apparent from Table 3, it was confirmed that the fibers obtained in Examples of the present invention have favorable stress and elongation, and high toughness.

INDUSTRIAL APPLICABILITY

The artificial polypeptide fiber of the present invention can be used suitably as reinforcing fibers of resin and metal, a composite material, an injection molding, etc. The uses can be applied to a transport machine member such as a car, and a reinforcing fiber of a tire. Moreover, it can be applied to a fishing line, strings of tennis and badminton rackets, a string of a violin, a bowstring of a violin, and artificial hair. It can be in a form of a yarn, a cotton, a weave, a knit, a braid, a nonwoven fabric, etc.

DESCRIPTION OF REFERENCE NUMERALS

1 extrusion process
2, 30 undrawn-yarn production process
3, 40 wet-heat drawing process (first-stage drawing process)
4, 50 dry-heat drawing process (second-stage drawing process)
5, 39, 44 yarn roll
6, 32 spinning solution
7 storage tank
8 gear pump
9 spinneret
10 spinning-drawing apparatus
11, 35 coagulation liquid
12, 38 hot water
13, 15, 41, 45 supply nip roller
14, 16, 42, 46 take-up nip roller
17, 43 dry-heat drawing machine
18*a*-18*f* yarn guide
19 air gap
20, 34 coagulation liquid bath
21, 37 drawing bath
22, 47 guide
31 syringe
33 nozzle
36 undrawn yarn

SEQUENCE LISTING FREE TEXT

SEQ ID NOS: 1 to 7 amino acid sequence
SEQ ID NOS: 8 to 10 base sequence
SEQ ID NOS: 11 to 14 primer sequence

The invention claimed is:

1. A method for producing an artificial polypeptide fiber that is obtained by spinning a spinning solution containing a polypeptide derived from natural spider silk proteins and performing drawing of at least two stages, wherein the drawing of at least two stages includes a first-stage drawing in wet heat and a second-stage drawing in dry heat, and an ambient temperature at the time of the second-stage drawing is in a range from 170 to 270° C.

2. The method for producing an artificial polypeptide fiber according to claim 1, wherein drawing conditions for the first-stage drawing include a temperature of hot water of 70-90° C. and a draw ratio of 2 to 8 times.

3. The method for producing an artificial polypeptide fiber according to claim 1, wherein drawing conditions for the second-stage drawing include an ambient temperature of 170 to 230° C. and a draw ratio of 1.25 to 3 times.

4. The method for producing an artificial polypeptide fiber according to claim 1, wherein the spinning is performed by extruding the spinning solution containing a polypeptide in a coagulation liquid so as to obtain an undrawn yarn, and the undrawn yarn is subjected to the first-stage drawing in the coagulation liquid.

5. The method for producing an artificial polypeptide fiber according to claim 1, wherein a total draw ratio of the fiber is more than 5 times and 20 times or less.

6. The method for producing an artificial polypeptide fiber according to claim 1, wherein a draw ratio of the second-stage drawing is in a range from 1.25 to 3 times.

* * * * *

```
                          SEQUENCE LISTING

<160> NUMBER OF SEQ ID NOS: 14

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50


<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30


<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20
```

<210> SEQ ID NO 4
<211> LENGTH: 1154
<212> TYPE: PRT
<213> ORGANISM: Artificial
<220> FEATURE:
<223> OTHER INFORMATION: recombinant spider silk protein ADF3KaiLargeNRSH1

<400> SEQUENCE: 4

```
Met His His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
        355                 360                 365
```

```
Pro Gly Ala Ser Ala Ala Ala Ala Ala Ala Gly Gly Tyr Gly Pro Gly
    370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
        435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
    530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
        595                 600                 605

Gln Gly Pro Tyr Gly Pro Gly Ala Ser Ala Ala Ala Ala Ala Ala Gly
    610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Ala Gly Gly Asn Gly
                645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
    690                 695                 700

Pro Tyr Gly Pro Gly Ala Ser Ala Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
    770                 775                 780
```

```
Ala Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
        835                 840                 845

Gly Ala Ser Ala Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
                885                 890                 895

Ala Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln  Gly Pro Gly Gln Gln  Gly Pro Gly
        995                 1000                 1005

Gln Gln  Gly Pro Gly Gln Gln  Gly Pro Tyr Gly Pro  Gly Ala Ser
    1010                 1015                 1020

Ala Ala  Ala Ala Ala Ala Gly  Gly Tyr Gly Pro Gly  Ser Gly Gln
    1025                 1030                 1035

Gln Gly  Pro Gly Gln Gln Gly  Pro Gly Gln Gln Gly  Pro Gly Gly
    1040                 1045                 1050

Gln Gly  Pro Tyr Gly Pro Gly  Ala Ala Ser Ala Ala  Val Ser Val
    1055                 1060                 1065

Gly Gly  Tyr Gly Pro Gln Ser  Ser Ser Val Pro Val  Ala Ser Ala
    1070                 1075                 1080

Val Ala  Ser Arg Leu Ser Ser  Pro Ala Ala Ser Ser  Arg Val Ser
    1085                 1090                 1095

Ser Ala  Val Ser Ser Leu Val  Ser Ser Gly Pro Thr  Lys His Ala
    1100                 1105                 1110

Ala Leu  Ser Asn Thr Ile Ser  Ser Val Val Ser Gln  Val Ser Ala
    1115                 1120                 1125

Ser Asn  Pro Gly Leu Ser Gly  Cys Asp Val Leu Val  Gln Ala Leu
    1130                 1135                 1140

Leu Glu  Val Val Ser Ala Leu  Val Ser Ile Leu
    1145                 1150


<210> SEQ ID NO 5
<211> LENGTH: 660
<212> TYPE: PRT
<213> ORGANISM: Artificial
<220> FEATURE:
<223> OTHER INFORMATION: recombinant spider silk protein ADF3Kai
```

<400> SEQUENCE: 5

```
Met His His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
        355                 360                 365

Pro Gly Ala Ser Ala Ala Ala Ala Ala Ala Gly Gly Tyr Gly Pro Gly
    370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
```

```
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
        435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
    530                 535                 540

Val Gly Gly Tyr Gly Pro Gln Ser Ser Ser Val Pro Val Ala Ser Ala
545                 550                 555                 560

Val Ala Ser Arg Leu Ser Ser Pro Ala Ala Ser Ser Arg Val Ser Ser
                565                 570                 575

Ala Val Ser Ser Leu Val Ser Ser Gly Pro Thr Lys His Ala Ala Leu
            580                 585                 590

Ser Asn Thr Ile Ser Ser Val Val Ser Gln Val Ser Ala Ser Asn Pro
        595                 600                 605

Gly Leu Ser Gly Cys Asp Val Leu Val Gln Ala Leu Leu Glu Val Val
    610                 615                 620

Ser Ala Leu Val Ser Ile Leu Gly Ser Ser Ser Ile Gly Gln Ile Asn
625                 630                 635                 640

Tyr Gly Ala Ser Ala Gln Tyr Thr Gln Met Val Gly Gln Ser Val Ala
                645                 650                 655

Gln Ala Leu Ala
            660


<210> SEQ ID NO 6
<211> LENGTH: 1183
<212> TYPE: PRT
<213> ORGANISM: Artificial
<220> FEATURE:
<223> OTHER INFORMATION: recombinant spider silk protein ADF3KaiLarge

<400> SEQUENCE: 6

Met His His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
```

-continued

```
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
        355                 360                 365

Pro Gly Ala Ser Ala Ala Ala Ala Ala Ala Gly Gly Tyr Gly Pro Gly
    370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
        435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525
```

```
Gly Gly Gln Gly Pro Tyr Gly Pro Gly Ala Ala Ser Ala Ala Val Ser
    530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
        595                 600                 605

Gln Gly Pro Tyr Gly Pro Gly Ala Ser Ala Ala Ala Ala Ala Ala Gly
    610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Ala Gly Gly Asn Gly
                645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
    690                 695                 700

Pro Tyr Gly Pro Gly Ala Ser Ala Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
    770                 775                 780

Ala Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
        835                 840                 845

Gly Ala Ser Ala Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
                885                 890                 895

Ala Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940
```

```
Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln  Gly Pro Gly Gln Gln  Gly Pro Gly
        995                 1000                 1005

Gln Gln  Gly Pro Gly Gln Gln  Gly Pro Tyr Gly Pro  Gly Ala Ser
    1010                 1015                 1020

Ala Ala  Ala Ala Ala Ala Gly  Gly Tyr Gly Pro Gly  Ser Gly Gln
    1025                 1030                 1035

Gln Gly  Pro Gly Gln Gln Gly  Pro Gly Gln Gln Gly  Pro Gly Gly
    1040                 1045                 1050

Gln Gly  Pro Tyr Gly Pro Gly  Ala Ala Ser Ala Ala  Val Ser Val
    1055                 1060                 1065

Gly Gly  Tyr Gly Pro Gln Ser  Ser Ser Val Pro Val  Ala Ser Ala
    1070                 1075                 1080

Val Ala  Ser Arg Leu Ser Ser  Pro Ala Ala Ser Ser  Arg Val Ser
    1085                 1090                 1095

Ser Ala  Val Ser Ser Leu Val  Ser Ser Gly Pro Thr  Lys His Ala
    1100                 1105                 1110

Ala Leu  Ser Asn Thr Ile Ser  Ser Val Val Ser Gln  Val Ser Ala
    1115                 1120                 1125

Ser Asn  Pro Gly Leu Ser Gly  Cys Asp Val Leu Val  Gln Ala Leu
    1130                 1135                 1140

Leu Glu  Val Val Ser Ala Leu  Val Ser Ile Leu Gly  Ser Ser Ser
    1145                 1150                 1155

Ile Gly  Gln Ile Asn Tyr Gly  Ala Ser Ala Gln Tyr  Thr Gln Met
    1160                 1165                 1170

Val Gly  Gln Ser Val Ala Gln  Ala Leu Ala
    1175                 1180
```

<210> SEQ ID NO 7
<211> LENGTH: 24
<212> TYPE: PRT
<213> ORGANISM: Artificial
<220> FEATURE:
<223> OTHER INFORMATION: His tag and start codon

<400> SEQUENCE: 7

```
Met His His His His His His His His His His Ser Ser Gly Ser Ser
1               5                   10                  15

Leu Glu Val Leu Phe Gln Gly Pro
            20
```

<210> SEQ ID NO 8
<211> LENGTH: 1983
<212> TYPE: DNA
<213> ORGANISM: Artificial
<220> FEATURE:
<223> OTHER INFORMATION: recombinant DNA of spider silk protein gene ADF3Kai

<400> SEQUENCE: 8

```
atgcatcacc atcatcatca tcaccaccac cattcctcgg gctcatcctt ggaagtgtta     60

tttcaaggac cagcacgagc cggttcggga caacaagggc ctggccagca gggcccaggt    120
```

```
caacaagggc caggacagca gggtccttat gggcccggcg caagcgcagc agctgcggcc    180

gctggtggct atggtcctgg ctccggtcaa cagggccctt cgcaacaagg tcccgggcag    240

caaggtcctg gtggccaggg tccctacggg ccgggggcga gtgcggcagc agccgctgca    300

ggcggttatg gtccaggaag cggacagcaa ggtccgggag gtcaaggtcc gtatggccca    360

ggctctagcg cggctgccgc tgccgcgggt ggcaacggac cagggagcgg acaacagggc    420

gcgggacaac agggtccagg acagcaaggc ccaggggcgt cggcggctgc agcggcggcc    480

ggaggctatg gacccggctc aggacaacag ggaccgggtc aacaaggacc cggtggccaa    540

ggcccctatg gcccgggcgc cagcgcggcc gcagccgccg cgggcgggta cggccccggt    600

agcggccagg gaccaggtca gcaggggcca ggaggtcagg gcccatacgg tccgggcgca    660

tccgcggcgg cggcagcggc aggtggctac ggtcccggaa gcggccaaca ggggccaggg    720

caacaaggac caggacaaca aggtcctggg ggccaaggac cgtatggacc aggagcatca    780

gctgcagccg cggcagctgg cggttacggt ccaggctacg gccagcaggg tccgggtcag    840

cagggaccgg gaggccaggg gccttatggc cctggcgctt ccgcagccag tgccgcttct    900

ggaggatacg ggccgggaag cggtcagcaa ggccctggcc aacaaggacc tggaggccaa    960

gggccctacg gcccaggagc ctcggcagcc gcagctgccg caggtgggta tgggccaggt   1020

agcgggcaac aagggccggg tcagcaagga ccggggcaac agggacctgg gcagcaagga   1080

cccgggggtc aaggcccgta cggacctggt gcgtctgcag ctgctgctgc ggctggtgga   1140

tatggtccgg gatcggggca gcagggtccc ggtcagcagg gccctggtca gcaagggcca   1200

ggccaacagg gacccggaca acaaggcccg ggtcaacagg gtcctggaca gcaggggccg   1260

ggccaacaag gccctgggca acagggtccg gggggacagg gggcctatgg gcctggcgca   1320

tctgccgccg ctggcgcagc cggtgggtac gggcctgggt caggtcaaca ggggcctggt   1380

caacaaggcc ccgggcaaca gggccccggc cagcaaggtc cagggcagca gggcccggga   1440

cagcaagggc ctggacaaca ggggcccgga cagcagggac cttacgggcc cggtgcgagc   1500

gcagcggccg ccgccgcagg gggatatggc cccggatcgg gccagcaggg accaggccag   1560

caaggacctg gccaacaggg cccgggggt cagggggcgt atggtcccgg cgctgcaagt    1620

gctgcagtgt ccgttggagg ttacggccct cagtcttcgt ctgttccggt ggcgtccgca   1680

gttgcgagta gactgtcttc acctgctgct tcatcgcgag tatcgagcgc tgtttcgtct   1740

cttgtctcgt cgggtcccac gaaacatgcc gccctttcaa atacgatttc atctgtagtg   1800

tcccaagtta gtgcaagtaa cccggggtta tccggatgcg acgttctcgt tcaggcactc   1860

ctagaagtag tatccgcgtt ggtgagcatc ttaggcagct cctcgatagg tcaaataaac   1920

tatggtgctt cagcccagta tacacagatg gtgggacaga gcgtcgcgca ggcattggct   1980

taa                                                                 1983
```

<210> SEQ ID NO 9
<211> LENGTH: 3552
<212> TYPE: DNA
<213> ORGANISM: Artificial
<220> FEATURE:
<223> OTHER INFORMATION: recombinant DNA of spider silk protein gene ADF3KaiLarge

<400> SEQUENCE: 9

```
atgcatcacc atcatcatca tcaccaccac cattcctcgg gctcatcctt ggaagtgtta     60

tttcaaggac cagcacgagc cggttcggga caacaagggc ctggccagca gggcccaggt    120
```

```
caacaagggc caggacagca gggtccttat gggcccggcg caagcgcagc agctgcggcc    180
gctggtggct atggtcctgg ctccggtcaa cagggccctt cgcaacaagg tcccgggcag    240
caaggtcctg gtggccaggg tccctacggg ccgggggcga gtgcggcagc agccgctgca    300
ggcggttatg gtccaggaag cggacagcaa ggtccgggag gtcaaggtcc gtatggccca    360
ggctctagcg cggctgccgc tgccgcgggt ggcaacggac cagggagcgg acaacagggc    420
gcgggacaac agggtccagg acagcaaggc ccaggggcgt cggcggctgc agcggcggcc    480
ggaggctatg gacccggctc aggacaacag ggaccgggtc aacaaggacc cggtggccaa    540
ggcccctatg gcccgggcgc cagcgcggcc gcagccgccg cgggcgggta cggccccggt    600
agcggccagg gaccaggtca gcaggggcca ggaggtcagg gcccatacgg tccgggcgca    660
tccgcggcgg cggcagcggc aggtggctac ggtcccggaa gcggccaaca ggggccaggg    720
caacaaggac caggacaaca aggtcctggg ggccaaggac cgtatggacc aggagcatca    780
gctgcagccg cggcagctgg cggttacggt ccaggctacg gccagcaggg tccgggtcag    840
cagggaccgg gaggccaggg gccttatggc cctggcgctt ccgcagccag tgccgcttct    900
ggaggatacg ggccgggaag cggtcagcaa ggccctggcc aacaaggacc tggaggccaa    960
gggccctacg gcccaggagc ctcggcagcc gcagctgccg caggtgggta tgggccaggt   1020
agcgggcaac aagggccggg tcagcaagga ccggggcaac agggacctgg gcagcaagga   1080
cccgggggtc aaggcccgta cggacctggt gcgtctgcag ctgctgctgc ggctggtgga   1140
tatggtccgg gatcggggca gcagggtccc ggtcagcagg gccctggtca gcaagggcca   1200
ggccaacagg gacccggaca acaaggcccg ggtcaacagg gtcctggaca gcaggggccg   1260
ggccaacaag gccctgggca acagggtccg gggggacagg gggcctatgg gcctggcgca   1320
tctgccgccg ctggcgcagc cggtgggtac gggcctgggt caggtcaaca ggggcctggt   1380
caacaaggcc ccgggcaaca gggccccggc cagcaaggtc cagggcagca gggcccggga   1440
cagcaagggc ctggacaaca ggggcccgga cagcagggac cttacgggcc cggtgcgagc   1500
gcagcggccg ccgccgcagg gggatatggc cccggatcgg gccagcaggg accaggccag   1560
caaggacctg gccaacaggg cccgggggt  cagggggcgt atggtcccgg cgctgcaagt   1620
gctgcagtgt ccgtttctag agcacgagcc ggttcgggac aacaagggcc tggccagcag   1680
ggcccaggtc aacaagggcc aggacagcag ggtccttatg ggcccggcgc aagcgcagca   1740
gctgcggccg ctggtggcta tggtcctggc tccggtcaac agggcccttc gcaacaaggt   1800
cccgggcagc aaggtcctgg tggccagggt ccctacgggc cgggggcgag tgcggcagca   1860
gccgctgcag gcggttatgg tccaggaagc ggacagcaag gtccgggagg tcaaggtccg   1920
tatggcccag gctctagcgc ggctgccgct gccgcgggtg gcaacggacc agggagcgga   1980
caacagggcg cgggacaaca gggtccagga cagcaaggcc caggggcgtc ggcggctgca   2040
gcggcggccg gaggctatgg acccggctca ggacaacagg gaccgggtca acaaggaccc   2100
ggtggccaag gcccctatgg cccgggcgcc agcgcggccg cagccgccgc gggcgggtac   2160
ggccccggta gcggccaggg accaggtcag caggggccag gaggtcaggg cccatacggt   2220
ccgggcgcat ccgcggcggc ggcagcggca ggtggctacg gtcccggaag cggccaacag   2280
gggccagggc aacaaggacc aggacaacaa ggtcctgggg gccaaggacc gtatggacca   2340
ggagcatcag ctgcagccgc ggcagctggc ggttacggtc caggctacgg ccagcagggt   2400
ccgggtcagc agggaccggg aggccagggg ccttatggcc ctggcgcttc cgcagccagt   2460
gccgcttctg gaggatacgg gccgggaagc ggtcagcaag gccctggcca acaaggacct   2520
```

```
ggaggccaag ggccctacgg cccaggagcc tcggcagccg cagctgccgc aggtgggtat   2580

gggccaggta gcgggcaaca agggccgggt cagcaaggac cggggcaaca gggacctggg   2640

cagcaaggac ccgggggtca aggcccgtac ggacctggtg cgtctgcagc tgctgctgcg   2700

gctggtggat atggtccggg atcggggcag cagggtcccg gtcagcaggg ccctggtcag   2760

caagggccag gccaacaggg acccggacaa caaggcccgg gtcaacaggg tcctggacag   2820

caggggccgg gccaacaagg ccctgggcaa cagggtccgg ggggacaggg ggcctatggg   2880

cctggcgcat ctgccgccgc tggcgcagcc ggtgggtacg ggcctgggtc aggtcaacag   2940

gggcctggtc aacaaggccc cgggcaacag ggcccgggcc agcaaggtcc agggcagcag   3000

ggcccgggac agcaagggcc tggacaacag gggcccggac agcagggacc ttacgggccc   3060

ggtgcgagcg cagcggccgc cgccgcaggg ggatatggcc ccggatcggg ccagcaggga   3120

ccaggccagc aaggacctgg ccaacagggc ccggggggtc aggggccgta tggtcccggc   3180

gctgcaagtg ctgcagtgtc cgttggaggt tacggccctc agtcttcgtc tgttccggtg   3240

gcgtccgcag ttgcgagtag actgtcttca cctgctgctt catcgcgagt atcgagcgct   3300

gtttcgtctc ttgtctcgtc gggtcccacg aaacatgccg ccctttcaaa tacgatttca   3360

tctgtagtgt cccaagttag tgcaagtaac ccggggttat ccggatgcga cgttctcgtt   3420

caggcactcc tagaagtagt atccgcgttg gtgagcatct taggcagctc ctcgataggt   3480

caaataaact atggtgcttc agcccagtat acacagatgg tgggacagag cgtcgcgcag   3540

gcattggctt aa                                                       3552
```

```
<210> SEQ ID NO 10
<211> LENGTH: 3465
<212> TYPE: DNA
<213> ORGANISM: Artificial
<220> FEATURE:
<223> OTHER INFORMATION: recombinant DNA of spider silk protein gene
      ADF3KaiLargeNRSH1

<400> SEQUENCE: 10

atgcatcacc atcatcatca tcaccaccac cattcctcgg gctcatcctt ggaagtgtta     60

tttcaaggac cagcacgagc cggttcggga caacaagggc ctggccagca gggcccaggt    120

caacaagggc caggacagca gggtccttat gggcccggcg caagcgcagc agctgcggcc    180

gctggtggct atggtcctgg ctccggtcaa cagggccctt cgcaacaagg tcccgggcag    240

caaggtcctg gtggccaggg tccctacggg ccgggggcga gtgcggcagc agccgctgca    300

ggcggttatg gtccaggaag cggacagcaa ggtccgggag gtcaaggtcc gtatggccca    360

ggctctagcg cggctgccgc tgccgcgggt ggcaacggac cagggagcgg acaacagggc    420

gcgggacaac agggtccagg acagcaaggc ccaggggcgt cggcggctgc agcggcggcc    480

ggaggctatg gacccggctc aggacaacag ggaccgggtc aacaaggacc cggtggccaa    540

ggcccctatg gcccgggcgc cagcgcggcc gcagccgccg cgggcgggta cggccccggt    600

agcggccagg gaccaggtca gcaggggcca ggaggtcagg gcccatacgg tccgggcgca    660

tccgcggcgg cggcagcggc aggtggctac ggtcccggaa gcggccaaca ggggccaggg    720

caacaaggac caggacaaca aggtcctggg ggccaaggac cgtatggacc aggagcatca    780

gctgcagccg cggcagctgg cggttacggt ccaggctacg gccagcaggg tccgggtcag    840

cagggaccgg gaggccaggg gccttatggc cctggcgctt ccgcagccag tgccgcttct    900

ggaggatacg ggccgggaag cggtcagcaa ggccctggcc aacaaggacc tggaggccaa    960
```

```
gggccctacg gcccaggagc ctcggcagcc gcagctgccg caggtgggta tgggccaggt   1020
agcgggcaac aagggccggg tcagcaagga ccggggcaac agggacctgg gcagcaagga   1080
cccgggggtc aaggcccgta cggacctggt gcgtctgcag ctgctgctgc ggctggtgga   1140
tatggtccgg gatcggggca gcagggtccc ggtcagcagg gccctggtca gcaagggcca   1200
ggccaacagg gacccggaca acaaggcccg ggtcaacagg gtcctggaca gcaggggccg   1260
ggccaacaag gccctgggca acagggtccg gggggacagg gggcctatgg gcctggcgca   1320
tctgccgccg ctggcgcagc cggtgggtac gggcctgggt caggtcaaca ggggcctggt   1380
caacaaggcc ccgggcaaca gggccccggc cagcaaggtc cagggcagca gggcccggga   1440
cagcaagggc ctggacaaca ggggcccgga cagcagggac cttacgggcc cggtgcgagc   1500
gcagcggccg ccgccgcagg gggatatggc cccggatcgg gccagcaggg accaggccag   1560
caaggacctg gccaacaggg cccgggggt caggggccgt atggtcccgg cgctgcaagt   1620
gctgcagtgt ccgtttctag agcacgagcc ggttcgggac aacaagggcc tggccagcag   1680
ggcccaggtc aacaagggcc aggacagcag ggtccttatg ggcccggcgc aagcgcagca   1740
gctgcggccg ctggtggcta tggtcctggc tccggtcaac agggcccttc gcaacaaggt   1800
cccgggcagc aaggtcctgg tggccagggt ccctacgggc cgggggcgag tgcggcagca   1860
gccgctgcag gcggttatgg tccaggaagc ggacagcaag gtccgggagg tcaaggtccg   1920
tatggcccag gctctagcgc ggctgccgct gccgcgggtg gcaacggacc agggagcgga   1980
caacagggcg cgggacaaca gggtccagga cagcaaggcc caggggcgtc ggcggctgca   2040
gcggcggccg gaggctatgg acccggctca ggacaacagg gaccgggtca acaaggaccc   2100
ggtggccaag gcccctatgg cccgggcgcc agcgcggccg cagccgccgc gggcgggtac   2160
ggccccggta gcggccaggg accaggtcag caggggccag gaggtcaggg cccatacggt   2220
ccgggcgcat ccgcggcggc ggcagcggca ggtggctacg gtcccggaag cggccaacag   2280
gggccagggc aacaaggacc aggacaacaa ggtcctgggg gccaaggacc gtatggacca   2340
ggagcatcag ctgcagccgc ggcagctggc ggttacggtc caggctacgg ccagcagggt   2400
ccgggtcagc agggaccggg aggccagggg ccttatggcc ctggcgcttc cgcagccagt   2460
gccgcttctg gaggatacgg gccgggaagc ggtcagcaag gccctggcca acaaggacct   2520
ggaggccaag ggccctacgg cccaggagcc tcggcagccg cagctgccgc aggtgggtat   2580
gggccaggta gcgggcaaca agggccgggt cagcaaggac cggggcaaca gggacctggg   2640
cagcaaggac ccgggggtca aggcccgtac ggacctggtg cgtctgcagc tgctgctgcg   2700
gctggtggat atggtccggg atcggggcag cagggtcccg gtcagcaggg ccctggtcag   2760
caagggccag gccaacaggg acccggacaa caaggcccgg gtcaacaggg tcctggacag   2820
caggggccgg gccaacaagg ccctgggcaa cagggtccgg ggggacaggg ggcctatggg   2880
cctggcgcat ctgccgccgc tggcgcagcc ggtgggtacg ggcctgggtc aggtcaacag   2940
gggcctggtc aacaaggccc cgggcaacag ggccccggcc agcaaggtcc agggcagcag   3000
ggcccgggac agcaagggcc tggacaacag gggcccggac agcagggacc ttacgggccc   3060
ggtgcgagcg cagcggccgc cgccgcaggg ggatatggcc ccggatcggg ccagcaggga   3120
ccaggccagc aaggacctgg ccaacagggc ccgggggtc aggggccgta tggtcccggc   3180
gctgcaagtg ctgcagtgtc cgttggaggt tacggccctc agtcttcgtc tgttccggtg   3240
gcgtccgcag ttgcgagtag actgtcttca cctgctgctt catcgcgagt atcgagcgct   3300
```

-continued

```
gtttcgtctc ttgtctcgtc gggtcccacg aaacatgccg ccctttcaaa tacgatttca   3360

tctgtagtgt cccaagttag tgcaagtaac ccggggttat ccggatgcga cgttctcgtt   3420

caggcactcc tagaagtagt atccgcgttg gtgagcatct tataa                   3465


<210> SEQ ID NO 11
<211> LENGTH: 20
<212> TYPE: DNA
<213> ORGANISM: Artificial
<220> FEATURE:
<223> OTHER INFORMATION: T7 promoter primer

<400> SEQUENCE: 11

taatacgact cactataggg                                                 20


<210> SEQ ID NO 12
<211> LENGTH: 27
<212> TYPE: DNA
<213> ORGANISM: Artificial
<220> FEATURE:
<223> OTHER INFORMATION: Rep Xba I primer

<400> SEQUENCE: 12

tctagaaacg gacactgcag cacttgc                                         27


<210> SEQ ID NO 13
<211> LENGTH: 28
<212> TYPE: DNA
<213> ORGANISM: Artificial
<220> FEATURE:
<223> OTHER INFORMATION: Xba I Rep primer

<400> SEQUENCE: 13

tctagagcac gagccggttc gggacaac                                        28


<210> SEQ ID NO 14
<211> LENGTH: 19
<212> TYPE: DNA
<213> ORGANISM: Artificial
<220> FEATURE:
<223> OTHER INFORMATION: T7 terminator primer

<400> SEQUENCE: 14

gctagttatt gctcagcgg                                                  19
```